United States Patent [19]

Medenica

[11] Patent Number: 5,846,758
[45] Date of Patent: Dec. 8, 1998

[54] METHOD FOR DIAGNOSING AUTOIMMUNE DISEASES

[75] Inventor: Rajko D. Medenica, Hilton Head Island, S.C.

[73] Assignee: His Excellency Ghassan I. Shaker, London, England

[21] Appl. No.: 565,408

[22] Filed: Nov. 30, 1995

[51] Int. Cl.$^6$ .............................. C12Q 1/02; C12Q 1/00; G01N 33/53; G01N 33/48

[52] U.S. Cl. ................................ 435/29; 435/4; 435/7.21; 435/7.23; 435/7.24; 436/63; 436/64; 436/805

[58] Field of Search ................... 435/29, 33, 40, 435/7.24, 4, 7.21, 7.23; 514/2; 436/536, 824, 63, 64, 805; 422/50

[56] References Cited

U.S. PATENT DOCUMENTS

| | | | |
|---|---|---|---|
| 4,420,461 | 12/1983 | Reckel et al. | 436/506 |
| 4,420,558 | 12/1983 | De Mey et al. | 435/28 |
| 4,595,654 | 6/1986 | Reckel et al. | 435/28 |
| 4,614,722 | 9/1986 | Pasula | 436/63 |
| 4,659,659 | 4/1987 | Dwek et al. | 435/18 |
| 4,743,540 | 5/1988 | Ralph et al. | 435/29 |
| 4,748,110 | 5/1988 | Paul | 435/29 |
| 5,147,785 | 9/1992 | Pasula | 436/501 |
| 5,162,990 | 11/1992 | Odeyale et al. | 364/413.1 |
| 5,192,537 | 3/1993 | Osband | 514/2 |
| 5,298,396 | 3/1994 | Kotzin et al. | 435/7.24 |
| 5,426,028 | 6/1995 | Levy et al. | 435/7.24 |
| 5,445,939 | 8/1995 | Anderson | 435/29 |
| 5,464,833 | 11/1995 | Nakai et al. | 514/2 |

OTHER PUBLICATIONS

McElrath et al, Proc. Natl. Acad. Sci., USA; vol. 86, pp. 675–679, Jan. 1989.

Jones, Carolyn J.P. and Jayson, Malcolm I., Chloroquine: its effect on leucocyte auto– and heterophagocytosis, *Annals of the Rheumatic Diseases*, Apr. 1984, vol. 43, No. 2, pp. 205–212.

Ericsson, Jan L.E., Holm, Göran, and Biberfeld, Peter, Increased Autophagocytosis in Renal Proximal Tubules during Experimental "Autoimmune" Nephrosis, *Virchows Archiv Abteilung B Zellpathologie–Cell Pathology*, (1969) vol. 2, pp. 74–84. Month not available.

*Primary Examiner*—Louise Leary
*Attorney, Agent, or Firm*—DeWitt Ross & Stevens SC

[57] ABSTRACT

A method for diagnosing autoimmune disease in mammals, including humans, is described. A blood sample is collected from a subject, and mononuclear white blood cells separated therefrom. The mononuclear cells then are cultured in vitro. Patients with autoimmune disease develop characteristic white cell aggregates with autophagocytosis in the culture. Mononuclear cells from normal patients do not exhibit this cell aggregation with autophagocytosis.

12 Claims, 3 Drawing Sheets

METHOD FOR DIAGNOSING AUTOIMMUNE DISEASES

FIELD OF THE INVENTION

The present invention is directed to a method for diagnosing autoimmune diseases.

DESCRIPTION OF THE PRIOR ART

The term "autoimmune diseases" is a generic term which describes a variety of illnesses in which a patient's body becomes the target of the patient's own immune system. As commonly used in the art, and as used herein, the term "autoimmune disease" includes such maladies as systemic lupus erythematosus, rheumatoid arthritis, psoriasis, phagoneuroglanulomatosis, Hashimoto's disease, myasthenia gravis, cirrhosis, and many other autoimmune conditions. All of these disease states share the common characteristic that the immune system of the patient mounts an immunogenic assault upon the patient's own body.

While there is presently no cure for most autoimmune diseases, there are treatment protocols which can ameliorate some of the suffering caused by many autoimmune diseases. The efficacy of these treatments is predicated largely upon accurate and early diagnosis of the autoimmune disease state of the patient. Consequently, there is an acute need for a diagnostic method which enables rapid, early, and accurate diagnosis of autoimmune disease states.

Several methods for diagnosing autoimmune diseases are described in the patent literature. For instance, Dwek et al., U.S. Pat. No. 4,659,659 describes a method for diagnosing diseases having an arthritic component such as rheumatoid arthritis and osteoarthritis. Dwek et al.'s diagnostic method hinges upon a determination of the amount of galactose in a sample of the patient's blood serum or plasma, or synovial fluid, or an Ig component or fraction thereof. The amount of galactose in a sample taken from the patient is compared to a sample taken from a normal, healthy individual to determine if a galactose deficiency exists in the patient.

Patents to Pasula, U.S. Pat. Nos. 4,614,722 and 5,147,785, describe methods for measuring the degree of reaction between antigens and leukocyte cellular antibodies, and the degree of reaction between a foreign entity and white blood cells, respectively. Briefly, the '722 patent describes a method for the objective determination of the degree of reaction between a suspected allergen and a blood sample. A blood sample is taken from a patient and separated into a control sample and a test sample. A suspected allergen is added to the test sample, along with a lysing agent to disintegrate the red blood cells in the sample. A lysing agent alone is introduced into the control sample. The white blood cell count and the cellular distribution of both the control sample and the test sample are then taken. Comparison of the white blood cell count in the test sample versus the white blood cell count in the control sample indicates whether the white blood cells reacted to the putative antigen.

The Pasula '785 patent describes an essentially identical protocol in which the antigen which is introduced into the test sample has a predetermined relationship with a malady to be diagnosed. For instance, to test for the presence of a specific cancer, a monoclonal antibody specific to that cancer is added to the test sample. If the patient is suffering from that specific cancer, the leukocytes in the subject's blood will react with the added cancer antigen, and the normally observed reaction will take place.

An immunoassay for HTLV-III antigens is described in Paul, U.S. Pat. No. 4,748,110. This reference briefly describes the detection of HTLV-III antigen in vitro by lymphocyte isolation followed by tissue culture of the lymphocytes and their co-cultivation with a human T-cell line such as HT-9, which is susceptible to infection with HTLV-III. The presence of the HTLV-III antigen is then detected in the cell culture by testing for reverse transcriptase activity or by immunofluorescent or sandwich enzyme immunoassay techniques. The Paul reference goes on to describe a direct immunoassay procedure for the detection of HTLV-III antigen in biological samples.

Ralph et al., U.S. Pat. No. 4,743,540, describe a method to assay and diagnose common varied immunodeficiency syndrome. In this method, subsets of common varied immunodeficiency syndrome are detected by exposing peripheral blood from patients suffering from the malady to various B-cell stimulatory factors. Distinct subsets of the syndrome are identified by the response of the peripheral blood cells to the various stimulatory factors. These subsets of common varied immunodeficiency syndrome aid in determining a further course of therapy to treat a given patient.

A patent to DeMey et al., U.S. Pat. No. 4,420,558, describes the use of bright field light microscopy for characterizing sub-types of white blood cells. By labeling the white blood cells and their precursors with gold-labeled antibodies, specific subpopulations of lymphocytes can be determined by light microscopy. DeMay et al. have found that the quantitative determination of various T-lymphocyte and B-lymphocyte subpopulations is useful for autoimmune disease diagnostic purposes. DeMay et al. note that cataloging T-lymphocytes and B-lymphocyte sub-populations provides a measure of the immunoregulatory status of a given patient, aids in the diagnosis of white blood cell neoplasms, and proves useful in monitoring the response of patients to various treatments.

U.S. Pat. No. 5,298,396, to Kotzin et al., describes a method for identifying T-cell populations which are involved in various autoimmune diseases. Here, the T-cell sub-populations are classified according to specific V-$\beta$ characteristics. Kotzin et al. have found that a comparison of the V-$\beta$ characteristics of T-cells is indicative of autoimmune disorders. The V-$\beta$ characteristics of mononuclear cells from peripheral blood of a patient is accomplished by isolating the mononuclear cells, exposing the same to anti-CD3 antibodies, followed by culturing in the presence of interleukin-2. RNA from the cells is then isolated. cDNA transcripts of the RNA are then synthesized using reverse transcriptase. The extent of V-$\beta$ characteristics of the cDNA transcripts is then determined via a PCR analysis using V-$\beta$-specific oligonucleotide primers.

A patent to Odeyale et al., U.S. Pat. No. 5,162,990, describes a method for quantifying macrophage phagocytosis by computer image analysis. Odeyale et al. note that increased susceptibility to infection has been associated with defective phagocytosis.

Reckel et al., U.S. Pat. Nos. 4,420,461 and 4,595,654, describe methods for detecting immune complexes. These two patents describe the production and use of a novel hybridoma which is capable of producing a monoclonal antibody which is specifically reactive with human Clq, but essentially non-cross reactive with human C1. The antibody selectively reacts with human Clq-containing complexes in the presence of human C1. The '461 patent describes a kit which contains capillary tubes which are filled with a mixture of Clq-coated GPO reagent cells, rabbit anti-Clq antibodies, and a precipitate from the biological fluid sample which contains immune complexes. The sample is allowed to react with the bound cells. The presence or absence of agglutination indicates whether the immune complexes are present in the sample. The '654 reference is drawn to the preparation of the hybridoma which produces the monoclonal antibody which is selectively reactive with human C1q.

None of the above references, taken alone or in any combination, are descriptive of the presently described and claimed method for diagnosing autoimmune diseases.

SUMMARY OF THE INVENTION

It is a principal aim of the present invention to provide an accurate and reliable method for diagnosing autoimmune disease in mammals, including humans, using a blood or bone marrow specimen taken from a mammalian subject.

It is a further aim of the present invention to provide a method for the diagnosis of autoimmune disease in mammals, including humans, which is predicated upon the autophagocytosic behavior of mononuclear cells in in vitro culture.

Yet a further aim of the present invention is to provide a method for the diagnosis of autoimmune disease in mammals, including humans, which does not require the use of expensive or esoteric reagents for its practice.

A still further aim of the present invention is to provide a method for the diagnosis of autoimmune disease in humans which is effective in confirming the presence of autoimmune disease by noting autophagocytosis in in vitro cultures of human blood cells or human bone marrow cells.

The present invention includes a method for diagnosing autoimmune disease in mammals, including humans, which comprises isolating a whole blood or bone marrow specimen from a mammalian subject. Optionally, mononuclear cells from the specimen may be isolated from the specimen. The whole blood or bone marrow specimen, or cells isolated therefrom are then cultured in vitro. The cells then are evaluated for the presence of autophagocytosis, along with the formation of cell aggregations. Evaluation is preferably performed via light microscopy. Such cell aggregations indicate the presence of autoimmune disease in the mammalian subject.

The present invention also includes a method for diagnosing such autoimmune diseases in humans as systemic lupus erythematosus, silicone implant-induced autoimmune reaction, immune deficiency syndrome, hepatitis C, Gulf War Syndrome, and Takayasu's arthritis, which comprises isolating a whole blood or bone marrow specimen from a human subject. Optionally, mononuclear cells from the specimen may be isolated from the specimen by ficoll-diatrizoate centrifugation. The whole blood or bone marrow specimen, or cells isolated therefrom are then cultured in vitro in a culture medium. The culture medium preferably comprises RPMI-1640 and 10% fetal calf serum. The cells are then evaluated by light microscopy for the presence of autophagocytosis, along with the formation of cell aggregations. Such cell aggregations indicate the presence of autoimmune disease in the human subject.

These and other objects, aims, and advantages of the present method to diagnose autoimmune disease will become apparent upon a complete reading of the "Detailed Description" and attached claims.

DETAILED DESCRIPTION OF THE INVENTION

Figure 1:
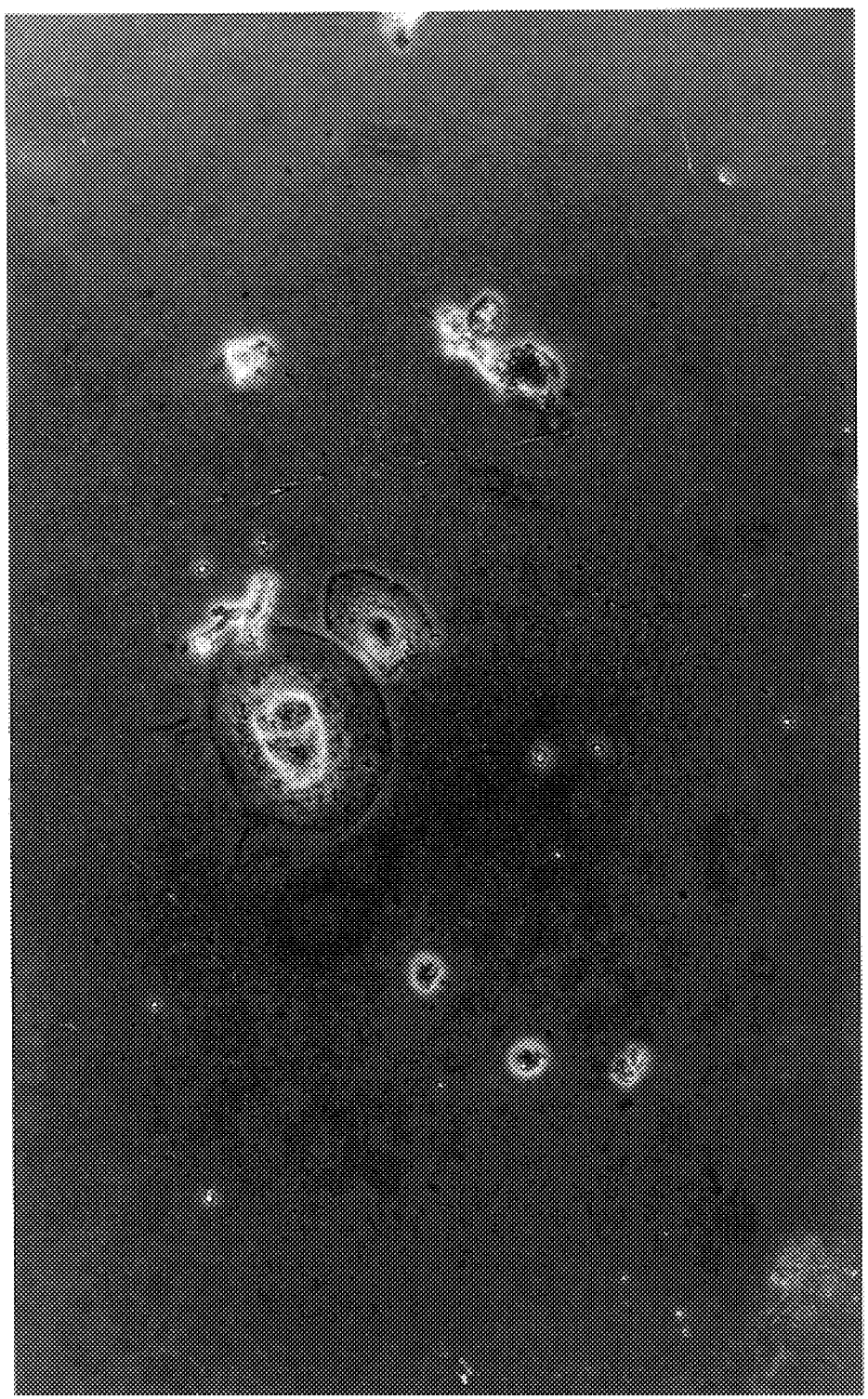
FIG. 1 is a light photomicrograph of a whole blood sample from a human patient suffering from systemic lupus erythematosus which displays the characteristic autophagocytosis phenomenon, with the formation of mononuclear cell aggregates.

The present method for diagnosing autoimmune disease is based upon a unique autophagocytosic phenomenon displayed by the white blood cells (WBCs) of individuals suffering from various immune disorders. This behavior is not displayed by the WBCs of healthy individuals. It has been found that in standard cell cultures, mononuclear cells of individuals suffering from autoimmune disease will begin to phagocytose other cells present within the cell culture. The autophagocytosis phenomenon appears in light microscopy as an aggregation within the cell culture. The aggregates are clusters of autophagocytosing cells surrounded by a ring of immunoblasts. During the course of therapy, the number of aggregates seen within a culture of a given patient is generally reduced, but is never eliminated entirely.

The present method for diagnosing autoimmune diseases is therefore predicated upon whether a given patient displays this autophagocytosic phenomenon. Normally patients do not.

In short, the present diagnostic method involves three essential steps, and one optional step. The three essential steps are as follows:

The first step is to isolate a specimen of whole blood or bone marrow from the subject to be tested. The second step is to culture the specimen in vitro for a sufficient amount of time to allow the aggregates to form. The third step is to evaluate the culture, preferably by light microscopy, to see if aggregates have formed in the culture. Presence of the cell aggregates indicates that the subject tested is suffering from an autoimmune disease. The cell aggregates are formed by the autophagocytosis of cells within the specimen.

An optional step is to separate mononuclear cells from the remainder of the cells in the whole blood or bone marrow specimen prior to in vitro culture. In this case, the culture contains only the mononuclear cells. Isolation of mononuclear cells from the specimen is most preferably done by ficoll-diatrizoate centrifugation, although other methods, such as differential lysis of the red blood cells within the specimen, function with equal success. The isolated mononuclear cells are cultured and evaluated in the same manner as a whole blood or bone marrow specimens.

As noted above, evaluation of the specimens is preferably performed using light microscopy.

Each of the above-described steps is described in full detail, below.

Specimen Collection

Whole blood is drawn from a patient by venipuncture, which is well known in the art. Approximately 10 ml of peripheral blood are drawn into a heparinized vacutainer tube (Becton-Dickinson). After the blood is drawn into the vacutainer tube, the tube is inverted several times to thoroughly mix the anti-coagulant with the drawn blood. Samples are refrigerated until needed. If the procedure is to be performed on a bone marrow sample, the bone marrow is collected using well known aseptic techniques.

Cells may also be harvested after plasmapheresis. Plasmapheresis is a well known procedure wherein blood is removed from a subject and the cells separated from the plasma portion of the whole blood. The corpuscles are then re-suspended in a buffered solution (such as Ringer's) and infused back into the subject. This results in a depletion of the subject's plasma proteins. An aliquot of the cells isolated during plasmapheresis can be used in the presently described diagnostic method.

Ficoll-Diatrizoate Centrifugation

Mononuclear cells are isolated from whole blood or bone marrow by the ficoll gradient density centrifugation method first described in 1968 by Boyum. In general, these procedures employ mixtures of a polysaccharide and a radio-opaque contrast medium. Such materials are readily available commercially, such as HISTOPAQUE-1077 (Coulter Corporation). HISTOPAQUE-1077 is a solution of ficoll (a synthetic copolymer of sucrose and epichlorhydrin) and sodium diatrizoate, adjusted to a density of $1.077 \pm 0.001$. This medium facilitates the rapid recovery of viable lymphocytes from small volumes of whole blood or bone marrow.

To perform the separation, anti-coagulated venous blood is layered onto a centrifuge tube containing HISTOPAQUE-1077. The tube is then centrifuged. The erythrocytes and granulocytes within the sample settle to the bottom of the tube. Lymphocytes and other mononuclear cells remain at the plasma-histopaque interface. After centrifugation the lymphocytes can be gently separated from the remainder of the ingredients in the centrifuged tube. An illustrative and typical procedure is as follows:

To 6–8 ml of anti-coagulated blood or bone marrow, add 10.0 ml of phosphate buffered saline (PBS) and mix well. Into a 16×75 ml sterile centrifuge tube, add 3.0 ml of HISTOPAQUE-1077 and bring to room temperature. Into the tube containing the histopaque, carefully layer 8–9 ml of the blood-PBS mixture onto the histopaque at an approximately 45 degree angle.

Centrifuge the tube at 400×g for 20 minutes at room temperature.

After centrifugation, carefully remove the upper layer from the opaque interface layer which contains the mononuclear cells. This is generally done with a sterile pipette. The upper layer can be discarded.

The opaque interface layer containing the mononuclear cells is transferred with a sterile pipette into another sterile centrifuge tube containing 5 ml of PBS. The contents of the centrifuged tube are gently mixed by inversion.

The centrifuge tube containing the mononuclear cells is then centrifuged at 250×g for 10 minutes. The supernate is again removed and discarded.

The lymphocyte pellet is again resuspended in 5.0 ml of fresh PBS, and mixed by gentle aspiration with a sterile pipette. The tube is again centrifuged at 250×g for 10 minutes.

The supernate is removed and discarded, and the mononuclear are cells resuspended in 2.5 ml of RPMI 1640 media. The mononuclear cells are now ready for cell counting by a COULTER COUNTER (Coulter Corporation) or by manual methods.

Viability of the cells isolated in this fashion may be determined by treatment with trypan blue in conventional fashion. The purity of the cell population obtained by this procedure may be determined by performing a Romanowsky stain on a film or a cytospin slide of the isolated mononuclear cells. These procedures are conventional and well known in the art. If cell viability is low (i.e., less than 80%), the PBS solution may be replaced with a tissue culture medium such as RPMI 1640 fortified with 5% fetal calf serum (FCS).

Liquid Tissue Culture

Subculture refers to cultures derived from dispersed cells taken from a given tissue, a primary culture, or from a cell line or cell strain, by enzymatic, mechanical, or chemical disaggregation. Once a culture is established, it will need periodic medium replacement ("feeding") followed eventually by subculture ("splitting") if the cells are proliferating. In non-proliferating cultures, the medium will still need to be changed periodically as the cells continue to metabolize. The metabolizing cells will deplete some constituents of the medium, while other constituents of the medium will degrade spontaneously. Intervals between medium changes and between subcultures vary from one cell line to another depending on the rate of growth and metabolism of the cells.

In general, mononuclear cells are cultured in standard fashion using conventional media in the pH range of from 7.0 to 7.4. The general procedure is as follows: Prepare an aliquot of the mononuclear cells isolated by gradient centrifugation to a concentration of $1.0 \times 10^6$ cells/ml. Into a 25 cm$^2$ culture flask, place 1.0 ml of the cell aliquot and 4.0 ml of cell culture media containing fetal calf serum (FCS). The preferred culture media is RPMI-1640 1× fortified plus FCS. Loosely cover the culture flask and incubate at 37° C. in a humid 5% $CO_2$-enriched atmosphere.

In general, to feed existing cultures, the spent medium is simply replaced with fresh medium. For adherent cell lines, the old medium is removed by pipetting, and the new medium gently added to the cell culture. For cells growing in suspension, the cell culture is first centrifuged, and the old medium removed by pipetting. The pellet is vortexed, and then resuspended in fresh media.

Splitting adherent cultures into subcultures is performed by washing the cells with EDTA-trypsin to gently loosen them from the bottom of the culture flask. A portion of the loosened cells is then transferred into a new flask along with fresh medium. The new flask is then incubated at 37° C. in a 5% $CO_2$-enriched atmosphere. Suspended cells are subcultured by pipetting a portion of the suspended cells into a new culture flask and adding new media.

Generally, the cells are cultured anywhere from about 7 to about 100 days. This culture period may be shortened if cell aggregation becomes readily apparent after a shorter period of time. Preferably, the cells are cultured for at least 30 days, or, more preferably still, at least 45 days. The cultured cells are evaluated on a regular basis for the presence of aggregates which are indicative of autoimmune disease.

Evaluation

Evaluation of the cells in culture is preferably performed by light microscopy. This is done by mounting an aliquot of the cultured cells to a standard glass slide in conventional fashion, and scanning the slide to determine if cell aggregates are present. The cells may be mounted to a gridded counting slide to manually determine the extent of cell aggregation. If desired, conventional staining techniques may be employed to distinguish various cell types and characteristics within the specimen.

Figure 2:
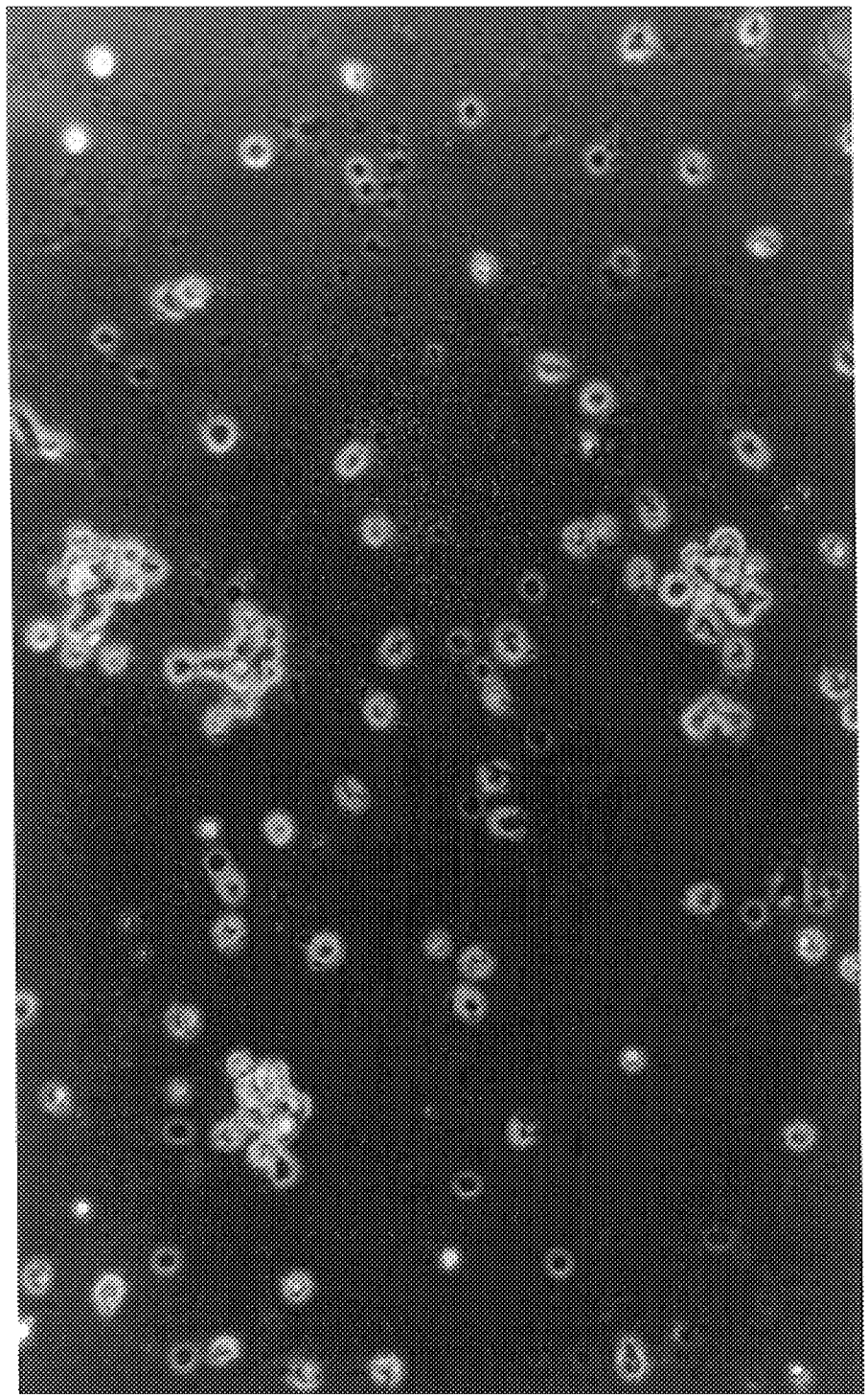
FIG. 2 is a light photomicrograph of a whole blood sample from a human patient suffering from Gulf War Syndrome which displays the characteristic autophagocytosis phenomenon, with the formation of mononuclear cell aggregates.
Figure 3:
FIG. 3 is a light photomicrograph of a whole blood sample from a human patient suffering from multiple chemical sensitivity syndrome which displays the characteristic autophagocytosis phenomenon, with the formation of mononuclear cell aggregates.

To illustrate the appearance of the cell aggregates, reference is made to FIGS. 1–3. FIG. 1 depicts the appearance of cell aggregates in a whole blood specimen from a human patient who was confirmed by other means to be suffering from systemic lupus erythematosus. The large mass to the left of the center of the photomicrograph of FIG. 1 is an aggregate of cells autophagocytosing a target cell.

FIG. 2 depicts the appearance of at least four aggregates of autophagocytosing cells from a whole blood specimen taken from a Gulf War veteran suffering from Gulf War Syndrome. This autoimmune ailment, which remains poorly characterized, first appeared in significant numbers in veterans of the Gulf War conflict in Kuwait and Iraq, from which it got its name. Its etiology remains unknown. Dispersed amongst a large number of unaggregated cells, four aggregates are clearly visible in the center and lower left portions of the photomicrograph.

FIG. 3 depicts the appearance of a number of cell aggregates from a human patient suffering from multiple chemical sensitivity syndrome. This autoimmune ailment is characterized by systemic sensitivity to a wide array of chemical entities. A particularly prominent aggregation can be seen in the lower right portion of this photomicrograph.

EXPERIMENTAL EXAMPLES

The following experimental examples were taken from human patients in a clinical setting. The examples are for illustrative purposes only to aid in a clear understanding of the present invention. The examples do not limit the diagnostic method described and claimed herein in any fashion.

The blood and bone marrow samples of the following examples were collected, cultured, and examined in the same fashion as described immediately above. One or more blood or bone marrow specimens were aseptically gathered from each patient. The mononuclear cells from within each specimen were then isolated by gradient centrifugation and cultured in the manner described above. Evaluation of the cell cultures for autophagocytosis with the formation of cell aggregates was performed by manual examination under light microscopy.

Patient No. 1

1.a. (Test performed on Day 11 of culture)
  Diagnosis: Systemic lupus erythematosus
  Specimen type: Whole blood
  Specimen evaluation: Blood in culture media.
  Viability: $1.8 \times 10^6$ cells/ml; 100% viability.
  Cytology: Normal peripheral smear.
  Morphology of the tissue culture: Clearly pronounced cell aggregations; aggregates appear as if one cell is trying to phagocytose the surrounding cells. Cell aggregation confirms original diagnosis of lupus.
1.b. (Test performed on Day 18 of culture)
  Diagnosis: Systemic lupus erythematosus
  Specimen type: Whole blood
  Specimen evaluation: Blood in culture media.
  Viability: $1.0 \times 10^6$ cells/ml; 100% viability.
  Cytology: Normal peripheral blood.
  Morphology of the tissue culture: This patient has active lupus with a considerable amount of immunocytes and rosetting phenomenon in the sample. The immunocytes are growing considerably, which indicates that this patient is not in complete remission.
1.c. (Test performed on Day 36 of culture)
  Diagnosis: Systemic lupus erythematosus
  Specimen type: Whole blood
  Specimen evaluation: Blood in culture media.
  Viability: $1.8 \times 10^6$ cells/ml; 100% viability.
  Cytology: Normal peripheral blood.
  Morphology of the tissue culture: There is a large number of reactive cells which are phagocytosing other cells and creating colonies.

Patient No. 2

2.a. (Test performed on Day 30 of culture)
  Diagnosis: Autoimmune-like syndrome/chemical sensitivity
  Specimen type: Plasmapheresis sediment
  Specimen evaluation: Plasmapheresis sediment in culture media.
  Viability: $0.7 \times 10^6$ cells/ml; 100% viability.
  Cytology: Rare white blood cells with many red blood cells present.
  Morphology of the tissue culture: Very rare macrophages are present; some immunocompetent and lupus phenomenon cells are seen, possibly due to some immune reaction. Poor cell growth with heavy red blood cell debris is observed.
2.b. (Test performed on Day 16 of culture, 3 months after 2.a.)
  Diagnosis: Autoimmune-like syndrome
  Specimen type: Plasmapheresis sediment
  Specimen evaluation: Plasmapheresis sediment in culture media.
  Viability: N/A
  Cytology: Normal finding.
  Morphology of the tissue culture: We see rosetting which is indicative of autoimmune disease.

Patient No. 3

3.a. (Test performed on Day 14 of culture)
  Preliminary diagnosis: Autoimmune reaction: silicone breast implants
  Specimen type: Whole Blood
  Macroscopic exam: Blood in culture media
  Viability: $1.0 \times 10^6$ cells/ml; 100% viability.
  Cytology: Normal peripheral blood.
  Morphology of the tissue culture: This patient suffers from a variant of autoimmune disease which developed after leakage of silicone breast implants. It was decided to evaluate blood in culture to see if the characteristic aggregation phenomenon is present. This sample has several autoimmune cells with characteristic hairy prolongation. The presence of these stimulated cells indicates that autoimmune disease may be present.
3.b (Test performed on Day 30 of culture)
  Diagnosis: Autoimmune reaction: silicone breast implants
  Specimen type: Whole Blood
  Macroscopic exam: Blood in culture media
  Viability: $1.0 \times 10^6$ cells/ml; 100% viability.
  Cytology: Normal peripheral blood.
  Morphology of the tissue culture: The aggregation phenomenon is clearly observed.

Patient No. 4

4.a (Test performed on Day 15 of culture)
  Diagnosis: Systemic lupus erythematosus
  Specimen type: Whole blood
  Specimen evaluation: Blood in culture media
  Viability: $1.0 \times 10^6$ cells/ml; 100% viability.
  Cytology: Normal peripheral blood.
  Morphology of the tissue culture: There is a considerable number of autoimmune cells present in this specimen. The cells have hairy prolongation. There are several islands of these cells present. A significant number of aggregations are present.

4.b (Test Performed on Day 20 of culture)
  Diagnosis: Systemic lupus erythematosus
  Specimen type: Whole blood
  Specimen evaluation: Blood in culture media
  Viability: $2.0 \times 10^6$ cells/ml; 100% viability.
  Cytology: Normal peripheral blood.
  Morphology of the tissue culture: A good number of immunocytes are present displaying the aggregation phenomenon. The phenomenon is characteristic for autoimmune disease.

Patient No. 5

Diagnosis: Gulf War syndrome
Specimen type: Whole blood
Specimen evaluation: Blood in culture media.
Viability: $2.2 \times 10^5$ cells/ml; 99% viability.
Cytology: Normal peripheral blood.
Morphology of the tissue culture: Patient presents with autoimmune symptomology. Patient is Gulf War veteran. A previously performed peripheral blood culture displayed the autoimmune phenomenon. This culture shows a considerable number of the autoimmune aggregates isolated in different islands. Cells surrounding the autoimmune aggregates have hairy prolongation.

Patient No. 6

Diagnosis: Autoimmune disease
Specimen type: Whole blood
Specimen evaluation: Blood in culture media.
Viability: $1.7 \times 10^6$ cells/ml; 100% viability.
Cytology: Normal peripheral blood.
Morphology of the tissue culture: White blood cells are seen phagocytosing red blood cells. This evaluation confirms the presence of autoimmune disease.

Patient No. 7

Diagnosis: Autoimmune reaction: silicone breast implants
Specimen type: Whole blood
Specimen evaluation: Blood in culture media
Viability: $1 \times 10^6$ cells/ml; 100% viability.
Cytology: Normal peripheral blood.
Morphology of the tissue culture: There is a large number of aggregated cells present in this specimen. We consider this tissue culture to be highly indicative of autoimmune disease.

Patient No. 8

Diagnosis: Hepatitis C
Specimen type: Whole blood
Specimen evaluation: Blood in culture media.
Viability: $6.3 \times 10^6$ cells/ml
Cytology: Normal peripheral blood.
Morphology of the tissue culture: There is a considerable number of cells present surrounding lupus-type cells. There is autoimmune aggregation activity present. Some of these cells are very suspicious cells that are seen in hepatoma.

Patient No. 9

Diagnosis: Autoimmune disease
Specimen type: Whole blood
Specimen evaluation: Blood in culture media.
Viability: $2.5 \times 10^6$ cells/ml; 100% viability.
Cytology: Normal peripheral blood.
Morphology of the tissue culture: A large number of immunocytes are present. The cells display aggregation activity.

Patient No. 10

Diagnosis: Takayasu's arthritis
Specimen type: Plasmapheresis
Specimen evaluation: Plasma taken after plasmapheresis procedure.
Viability: $1.0 \times 10^5$ cells/ml; 67% viability.
Cytology: Normal plasma.
Morphology of the tissue culture: No observation of the rosetting phenomenon. There is one immunocyte present which indicates autoimmune disease.

Patient No. 11

Diagnosis: Immune deficiency syndrome
Specimen type: Whole Blood
Specimen evaluation: Blood in culture media
Viability: $1.0 \times 10^6$ cells/ml; 100% viability.
Cytology: Normal whole blood.
Morphology of the tissue culture: There are definite signs of the immunological phenomenon of phagocytosis. The cells are immunocytes and immunocompetent cells which have hairy prolongation.

Patient No. 12

Diagnosis: Gulf War syndrome
Specimen type: Bone Marrow
Specimen evaluation: Bone marrow in culture media.
Viability: $6.8 \times 10^6$ cells/ml; 100% viability.
Cytology: Normal bone marrow.
Morphology of the tissue culture: Autoimmune cells are present with the possibility of the phagocytosis.

Patient No. 13

Diagnosis: Cirrhosis of liver
Specimen type: Whole Blood
Specimen evaluation: White blood cells in culture media.
Viability: $1.0 \times 10^6$ cells/ml Cytology: Normal peripheral blood Morphology of the tissue culture: This patient suffers from hepatitis C and cirrhosis of liver. There is a large number of autoimmune competent cells with phagocytic expression. This is characteristic of autoimmune disease. This patient has definitely developed autoimmune disease.

Patient No. 14

Diagnosis: Autoimmune-like syndrome

Specimen type: Whole Blood

Specimen evaluation: White blood cells in culture media

Viability: $1.0 \times 10^6$ cells/ml; 100% viability

Cytology: Normal peripheral blood.

Morphology of the tissue culture: As expected, there is a large island with phagocytotic activity. This patient definitely has autoimmune disease.

Patient No. 15

Diagnosis: Systemic lupus erythematosus

Specimen type: Whole Blood

Specimen evaluation: Blood in culture media.

Viability: $1.0 \times 10^6$ cells/ml; 100% viability

Cytology: Normal peripheral blood.

Morphology of the tissue culture: The specimen is demonstrating a large number of the immunocytes. However, they are not as active as in the early phase of the disease. The presence of the immunocytes and aggregation phenomenon has been reduced considerably in this specimen. Patient seems to be in remission of systemic lupus.

Patient No. 16

Diagnosis: Autoimmune disease

Specimen type: Whole Blood

Specimen evaluation: Whole blood in culture media

Viability: $1.0 \times 10^6$ cells/ml; 100% viability

Cytology: Normal peripheral blood.

Morphology of the tissue culture: There is a large number of immunocytes present, and the autophagocytosis phenomenon is present. However, the autophagocytosis is much less prevalent than seen in a previous test. The patient is still not in remission, but has improved considerably since the first test.

It is understood that the present invention is not limited to the particular reagents, steps, or methods disclosed herein, but rather embraces all such forms thereof as come within the scope of the attached claims.

What is claimed is:

1. A method for diagnosing autoimmune disease in mammals comprising:
   a. isolating a whole blood or bone marrow specimen from a mammalian subject under sterile conditions;
   b. isolating mononuclear cells from the specimen under sterile conditions;
   c. culturing the mononuclear cells in vitro under sterile conditions;
   d. evaluating the cultured mononuclear cells for the presence of autophagocytosis wherein the cultured mononuclear cells are phagocytosing themselves, whereby the presence of autoimmune disease in the mammalian subject is diagnosed.

2. The method according to claim 1, wherein in step c) the mononuclear cells are cultured from 7 to 45 days.

3. The method according to claim 1, wherein in step c) the mononuclear cells are cultured for at least 30 days.

4. The method according to claim 1, wherein in step d) the cultured mononuclear cells are evaluated for the presence of autophagocytosis by light microscopy.

5. The method according to claim 1, wherein in step a) the specimen is isolated from a human subject.

6. The method according to claim 5, wherein in step b) the mononuclear cells are isolated by ficoll-diatrizoate centrifugation.

7. The method according to claim 5, wherein in step c) the mononuclear cells are cultured in a medium comprising RPMI-1640.

8. The method according to claim 7, wherein the mononuclear cells are cultured in a medium further comprising fetal calf serum.

9. The method according to claim 8, wherein the mononuclear cells are cultured in a medium comprising about 10% fetal bovine serum.

10. The method according to claim 9, wherein the mononuclear cells are cultured at about 37° C. in an atmosphere of about 5% carbon dioxide.

11. The method according to claim 5, wherein the autoimmune disease being diagnosed is selected from the group consisting of systemic lupus erythematosus, silicone implant-induced autoimmune reaction, immune deficiency syndrome, hepatitis C, Gulf War Syndrome, multiple chemical sensitivity syndrome, cirrhosis, and Takayasu's arthritis.

12. A method for diagnosing autoimmune disease in humans selected from the group consisting of systemic lupus erythematosus, silicone implant-induced autoimmune reaction, immune deficiency syndrome, hepatitis C, Gulf War Syndrome, multiple chemical sensitivity syndrome, cirrhosis, and Takayasu's arthritis comprising:
   a. isolating a whole blood or bone marrow specimen from a human subject under sterile conditions;
   b. isolating mononuclear cells from the specimen by ficoll-diatrizoate centrifugation under sterile conditions;
   c. culturing the mononuclear cells in vitro in a culture medium comprising RPMI-1640 and 10% fetal bovine serum under sterile conditions;
   d. evaluating the cultured mononuclear cells for the presence of autophagocytosis wherein the cultured mononuclear cells are phatocytosing themselves by light microscopy, whereby the presence of autoimmune disease in the human subject is diagnosed.

* * * * *